(12) United States Patent
Chen et al.

(10) Patent No.: US 8,975,234 B2
(45) Date of Patent: Mar. 10, 2015

(54) ANTI-BACTERIAL INFECTION, INFLAMMATION, AND LEUKEMIA COMPOSITION AND USE THEREOF

(75) Inventors: Lih-Geeng Chen, Kaohsiung (TW); Yen-Hsu Chen, Kaohsiung (TW); Chin Hsu, Kaohsiung (TW); Hsin-Ju Chien, Kaohsiung (TW); Shih-Han Kao, Kaohsiung (TW); Yu-Wei Chang, Kaohsiung (TW); Wan-Chun Huang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 1 day.

(21) Appl. No.: 13/354,496

(22) Filed: Jan. 20, 2012

(65) Prior Publication Data

US 2012/0190632 A1    Jul. 26, 2012

(30) Foreign Application Priority Data

Jan. 26, 2011  (TW) .............................. 100102873 A

(51) Int. Cl.
| | | |
|---|---|---|
| *A61K 31/70* | (2006.01) | |
| *A61K 31/7024* | (2006.01) | |
| *A61K 31/43* | (2006.01) | |
| *A61K 31/431* | (2006.01) | |
| *A61K 31/65* | (2006.01) | |
| *A61K 45/06* | (2006.01) | |

(52) U.S. Cl.
CPC ............. *A61K 31/7024* (2013.01); *A61K 31/43* (2013.01); *A61K 31/431* (2013.01); *A61K 31/65* (2013.01); *A61K 45/06* (2013.01)
USPC .......................................................... 514/25

(58) Field of Classification Search
USPC .......................................................... 514/25
See application file for complete search history.

(56) References Cited

U.S. PATENT DOCUMENTS 7,288,273 B1 * 10/2007 Feldman ......................... 424/776
2011/0105421 A1 * 5/2011 Mathee et al. ................... 514/29

* cited by examiner

*Primary Examiner* — Elli Peselev
(74) *Attorney, Agent, or Firm* — WPAT, P.C.; Anthony King; Kay Yang

(57) ABSTRACT

A method of inhibiting the growth of Gram-positive bacteria comprising administering an effective amount of Tellimagrandin II, its pharmaceutically acceptable salt, enantiomer, isomer or tautomer to a subject is provided. The Gram-positive bacteria comprise methicillin-resistant *Staphylococcus aureus*. A method of treating sepsis comprising administering an effective amount of Tellimagrandin II, its pharmaceutically acceptable salt, enantiomer, isomer or tautomer to a subject is also provided. A method of treating leukemia comprising administering an effective amount of Tellimagrandin II, its pharmaceutically acceptable salt, enantiomer, isomer or tautomer to a subject is further provided.

13 Claims, 18 Drawing Sheets

TG II (40 µg/mL)        —                +

10 min 24 hr

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: ftsZ forward primer
<220> FEATURE:
<221> NAME/KEY: misc_feature
<222> LOCATION: (1)..(20)

<400> SEQUENCE: 1
ttactggtgg cgagtcattg                                               20

<210> SEQ ID NO 2
<211> LENGTH: 20
<212> TYPE: DNA
<213> ORGANISM: Artificial
<220> FEATURE:
```

```
<223> OTHER INFORMATION: ftsZ reverse primer
<220> FEATURE:
<221> NAME/KEY: misc_feature
<222> LOCATION: (1)..(20)

<400> SEQUENCE: 2
tttacgcttg ttccgaatcc                                                    20

<210> SEQ ID NO 3
<211> LENGTH: 21
<212> TYPE: DNA
<213> ORGANISM: Artificial
<220> FEATURE:
<223> OTHER INFORMATION: mecA forward primer
<220> FEATURE:
<221> NAME/KEY: misc_feature
<222> LOCATION: (1)..(21)

<400> SEQUENCE: 3
ctgctatcca ccctcaaaca g                                                  21

<210> SEQ ID NO 4
<211> LENGTH: 22
<212> TYPE: DNA
<213> ORGANISM: Artificial
<220> FEATURE:
<223> OTHER INFORMATION: mecA reverse primer
<220> FEATURE:
<221> NAME/KEY: misc_feature
<222> LOCATION: (1)..(22)

<400> SEQUENCE: 4
tcttcgttac tcatgccata ca                                                 22
```

ANTI-BACTERIAL INFECTION, INFLAMMATION, AND LEUKEMIA COMPOSITION AND USE THEREOF

FIELD OF THE INVENTION

The present invention is directed to the use of Tellimagrandin II for the inhibition of Gram-positive bacteria growth, the anti-inflammation and the treatment of leukemia.

BACKGROUND OF THE INVENTION

Anti-Bacterial Infection

*Staphylococcus aureus* (SA) belongs to Gram-positive cocci, and is the common cause of clinical infections (e.g. skin trauma infection, food poisoning, septic shock and the like) and nosocomial infection. The discovery of Penicillin in 1950 brought a big breakthrough in the fighting against *Staphylococcus aureus*. However, Penicillin-resistant *Staphylococcus aureus* was isolated and identified in the late 1950. When other antibiotics such as Methicillin and Oxacillin were just developed, the *Staphylococcus aureus* with drug resistance against these two compounds emerged due to antibiotic misuse, which also known as Methicillin-resistant *Staphylococcus aureus* (MRSA). The threat of antibiotic resistance increased rapidly. Until 2003, MRSA was counted for 50% *Staphylococcus aureus* isolated from clinical sample in US. According to the analysis by Center for Disease Control (R.O.C.) in 2009, MRSA is also the leading cause of nosocomial infection in Taiwan (70-80%).

To resist antibiotics, *Staphylococcus aureus* exhibits several underlying mechanisms. Producing β-lactamase is the main mechanism of β-lactam antibiotic (such as Penicillin, Methicillin, and Oxacillin) resistance. However, the β-lactam antibiotic resistance of *Staphylococcus aureus* is mainly contributed by mecA gene expression rather than β-lactamase containing. The mecA gene encodes an additional protein called Penicillin-binding protein 2a (PBP2a or PBP2'), which has low affinity to β-lactam. PBP2a makes it difficult for Methicillin to bind with and react on *Staphylococcus aureus*.

The clinical indication of Methicillin resistant *Staphylococcus aureus* is minimum inhibitory concentration (MIC) of Oxacillin ≥4 μg/mL and containing the mecA gene or the product thereof. Otherwise, many Methicillin-resistant *Staphylococcus aureus* in European exhibit resistance to Tetracycline antibiotics.

In addition to the drug resistance, *Staphylococcus aureus* tends to form biofilm and causes clinical conductor infection. Therefore, development of biofilm inhibitory compound will significantly decrease conductor and other clinical-related infection.

The anti-bacterial effects of some tannins natural extracts had been reported. Tannins can be classified into two categories, hydrolysable tannins and condensed tannins Polyphenol is one kind of tannins and generally presents in various fruits, vegetables and red wine. The most common functions of polyphenol are anti-oxidation, antifungal, antibacterial and the like. Polyphenol derived from natural extracts has low cytotoxicity to normal cell but high cytotoxicity to cancer cell. Some studies report that polyphenol natural extracts can also kill MRSA. These natural extracts can be roughly divided into three classes: polyphenol with low molecular weight, oxidizing product-producing polyphenol and polyphenol with high molecular weight. It had been reported that the antibacterial effect of polyphenol is proportional to its molecular weight, especially (–)-Epicatechin gallate (ECg), Corilagin and Tellimagrandin I (TG I). There are papers indicate that various polyphenol natural extracts or tannins natural extracts have synergistically bactericidal effect with β-lactam antibiotic; for instance, ECg can reduces permeability and D-alanylation of cell wall. In addition, genetic studies point out neurologic drug, Thioridazine, also can restore the sensitivity of Methicillin-resistant *Staphylococcus aureus*. The above effect acts through inhibition of mecA gene expression and PBP2a protein production. However, Thioridazine is rarely used nowadays due to its toxicity.

Drug resistance severity of Methicillin-resistant *Staphylococcus aureus* infection grows these days, and it takes a long time for research and development of new antibiotic. Natural extracts have advantages of low toxicity to normal cell, little harm to human body and even other therapeutic effects.

The derivative of TG I, Tellimagrandin II (TG II), has one more functional group than TG I, gallic acid. In polyphenols, gallic acid resists fungous and virus infection and protects cells from oxidative stress. Moreover, gallic acid also has better cancer cell-killing ability. Tellimagrandin II can be homogenously extracted from *Trapa natans* L. or *Rosa rugosa* Thunb. by acetone.

Anti-Inflammation

Sepsis, septic shock and multiple organ dysfunction syndrome (MODS/MOF) are major death causes of patients in the ICU. Although there is great progress in studies about the pathogenesis and therapy of sepsis and its complications, mortality rate of sepsis still shows poor improvement. In the statistical analysis of USA, there are 750 thousand sepsis cases every year, and only 50% to 70% of them can survive. Sepsis and its complications has been the 13th leading cause of death. They contribute to more than 600 death cases every day.

In the past decade, Gram-negative bacilli have been the most common pathogens of sepsis. Most Gram-negative bacilli are normal flora in gastrointestinal tract and spread to neighboring tissues under certain causes, for example, peritonitis secondary to perforated appendicitis and urinary tract infection by bacilli ascending perineum to urethra or bladder. The primary focus of sepsis usually occurs at lung, genitourinary tract, liver, gallbladder and gastrointestinal tract, skin or soft tissue. The primary focus cannot be identified for about 20-30% sepsis patients, especially those with cirrhosis, cancer and other chronic debilitating diseases.

Current studies on sepsis etiology and treatment indicate that sepsis etiology is closely related to lipopolysaccharides (LPS), also known as endotoxin, released from the cell wall of Gram-negative bacilli. When body cells are stimulated by microbial compositions such as lipopolysaccharide and endotoxin, complements, white blood cells and vascular endothelial cells will be activated by the release of cytokines, TNF, etc. When the immune system is activated by infection, NO, a regulator of blood vessel tone, is released in ample amount, interacting with superoxide anion to form peroxynitrite, which may be recombined to nitrate, to produce toxic hydroxyl ions or to facilitate the formation of destructive oxidizing peroxynitrous acid.

In addition, NO is vital in the regulation of some inflammatory diseases such as ulcerative colitis, psoriasis and sepsis. NO is formed when nitrix oxide synthases (NOS) regulates the oxidation of L-Arginine. NOS are divided into two categories. One is calcium-dependent constitutive NOS (cNOS) such as neuronal cNOS (NOS1) and endothelial cNOS (NOS3). The other is calcium-independent inducible NOS (NOS2), released mostly by macrophages, liver cells, and cartilage cells.

Besides NOS2, cyclooxygenase II (COX-2) also plays an important role in the early phase of inflammatory response. Like COX-1, COX-2 hydrolyzes arachidonic acid to prostaglandin endoperoxide $H_2$ ($PGH_2$), the precursor of $PGD_2$, $PGE_2$, $PGI_2$, etc. Unlike COX-1, which is constitutive in most animal cells, COX-2 expression must be stimulated by endotoxin and cytokines such as IL-1, IL-2 or TNF-α. COX-2 regulates blood flow velocity, edema and body sensitivity to pain in an inflammatory response.

According to researches, heme oxygenase-1 (HO-1) is anti-inflammatory and decreases death rate during sepsis. HO-1 decomposes heme into CO and divalent iron. CO regulates macrophages to inhibit the occurrence and worsening of inflammatory response. A divalent iron binds to free radicals and therefore is anti-oxidizing. HO-1 performs multiple functions such as vasodilatation to protect human body against inflammatory mechanism in inflammatory response.

Tellimagrandin II belongs to the hydrolysable tannin of polyphenolic compound. Polyphenolic compound is extracted from most advanced plants. Tannin exists in animal skin, facilitates protein precipitation and serves as a superb metal chelating agent. Because it can remove free radicals, it may be used to alleviate the overoxidation induced by inflammation in organism.

Anti-Leukemia

Leukemia is also known as cancer of blood. Programmed cell death is a part of normal cell physiology and apoptosis is the programmed cell death under inappropriate living condition. The initial identification of apoptosis or other death of cell such as necrosis in experiments is by cell morphogenesis with a microscope. The major difference between apoptosis and other death of cell is the more complete cell membrane at the later stage to prevent serum and organelles from leaking, resulting in unique apoptotic bodies.

The process also includes the breakdown of shape-maintaining proteinaceous cytoskeleton by a specific protease, nucleic acid fragmentation, chromatin condensation, and blebs on cell membrane. There have been many researches published about cancer cell inhibition of polyphenolic compounds. The inhibitions of growth in human leukemia cells, HL-60, and cell cycle stagnation have been validated. The author observed programmed apoptosis in cells treated with tannic acid at certain concentrations. Finally, the variation in related protein was used to predict that apoptosis induced by internal signaling transduction, mostly by mitochondria. There have been more researches on tea polyphenols about its apoptosis-inducing mechanism in leukemia cells.

The causes of apoptosis are different and divided into internal and external paths. The internal path is triggered when mitochondria membrane potential alters, apoptotic protein Bcl-2 decreases and Bax increases as a result of the induced increase in cell reactive oxygen species or other unfavorable factors to cell survival. Cytochrom C in mitochondria is released into cytoplasm outside the mitochondrial membrane, inducing the following activation of apoptotic protein, mostly Caspase-9. Finally cell DNA fragmentizes and apoptosis is completed. The external path is triggered by the existence of a death factor, such as Fas-L. It binds to Fas receptor before activating apoptotic proteins, mostly Caspase-8, and then programmed apoptosis.

Many researches have validated that tannin is related to the inhibition of tumor cell growth. Tannin compound is divided into hydrolyzable tannins and Condensed tannins. Purified plant polyphenols belongs to one type of hydrolyzable tannins. It's currently known to relate to the programmed death in tumor cells mediated by reactive oxygen species.

SUMMARY OF THE INVENTION

Figure 1:
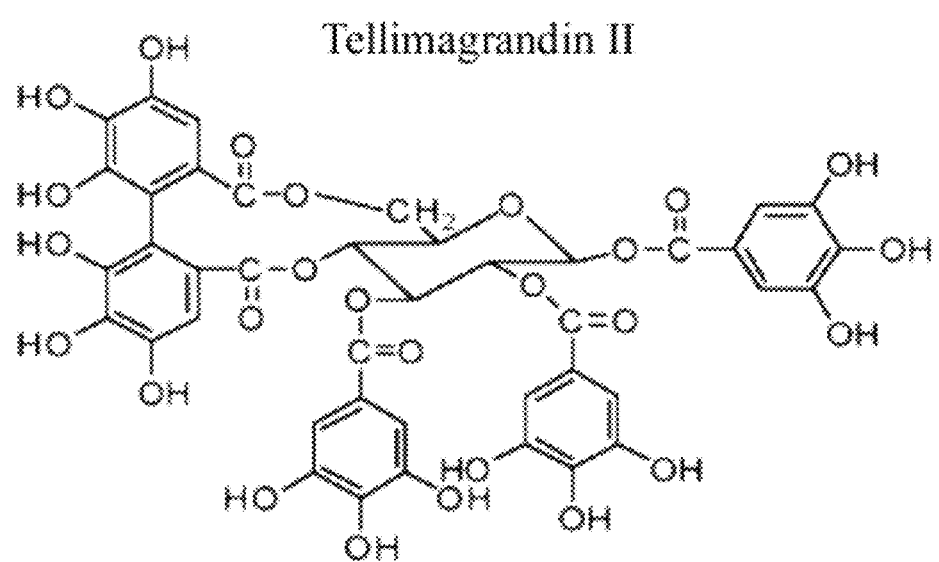
FIG. 1 shows the structure of Tellimagrandin II (TG II).

To overcome *Staphylococcus aureus* infection, sepsis and leukemia, the present invention provides a method of inhibiting the growth of Gram-positive bacteria comprising administering an effective amount of Tellimagrandin II, its pharmaceutically acceptable salt, enantiomer, isomer or tautomer to a subject. The Gram-positive bacteria comprise methicillin-resistant *Staphylococcus aureus*. The present invention also provides a method of anti-inflammation, such as sepsis, comprising administering an effective amount of Tellimagrandin II, its pharmaceutically acceptable salt, enantiomer, isomer or tautomer to a subject. The present invention further provides a method of treating leukemia comprising administering an effective amount of Tellimagrandin II, its pharmaceutically acceptable salt, enantiomer, isomer or tautomer to a subject.

DETAILED DESCRIPTION OF THE INVENTION

As used herein, the term "Tellimagrandin II" refers to a natural polyphenol compound which is extracted from, such as but not limited to, the shell of *Trapa hispinosa*.

As used herein, the term "subject" refers to a mammal, more preferably a human. Mammals include, but are not limited to, humans, primates, farm animals, sport animals, rodents and pets.

As used herein, the term "a" or "an" is employed to describe category or species of antibiotic or element or component of the invention. This is done merely for convenience and to give a general sense of the invention. This description should be read to include one or at least one and the singular also includes the plural unless it is obvious that it is meant otherwise.

As used herein, the term "or" is employed to describe "and/or".

Accordingly, the present invention provides a method of inhibiting the growth of Gram-positive bacteria comprising administering an effective amount of Tellimagrandin II, its pharmaceutically acceptable salt, enantiomer, isomer or tautomer to a subject. In one embodiment, the method further comprises administering an effective amount of a β-lactam antibiotic or a polyketide antibiotic to the subject. In another embodiment, the bacteria are *Staphylococcus aureus* or methicillin-resistant *Staphylococcus aureus*.

In one embodiment, the Tellimagrandin II acts synergistically with β-lactam antibiotic or polyketide antibiotic to inhibit the growth of methicillin-resistant *Staphylococcus aureus*. In another embodiment, the β-lactam antibiotic comprises, but not limited to, penicillins, for example, benzathine penicillin, benzylpenicillin, phenoxymethylpenicillin, procaine penicillin, methicillin, oxacillin, nafcillin, cloxacillin, dicloxacillin, flucloxacillin, temocillin, amoxicillin, ampicillin, co-amoxiclav, azlocillin, carbenicillin, ticarcillin, mezlocillin, and piperacillin; cephalosporins, for example, cephalexin, cephalothin, cefazolin, cefaclor, cefuroxime, cefamandole, cefotetan, cefoxitin, ceftriaxone, cefotaxime, cefpodoxime, cefixime, ceftazidime, cefepime and cefpirome; carbapenems or penems, for example, imipenem, meropenem, penipenem, biapenem, ertapenem, faropenem and doripenem; monobactams, for example, aztreonam, tigemonam, nocardicin A and tabtoxinine-β-lactam; or β-lactamase inhibitor, such as clavulanic acid, tazobactam and sulbactam. In still another embodiment, the polyketide antibiotic comprises, but not limited to, tetracycline, doxycycline, minocycline, erythromycin, monensin A (rumensin), tylosin, narasin, rifamycin, cervimycin C, jadomycin B, kirromycin or mupirocin. In one embodiment, the β-lactam antibiotic is methicillin, oxacillin, nafcillin, cloxacillin, dicloxacillin, flucloxacillin, temocillin or amoxicillin. In another embodiment, the polyketide antibiotic is tetracycline, doxycycline or minocycline. In still another embodiment, the β-lactam antibiotic is oxacillin and the polyketide antibiotic is doxycycline.

In one embodiment, the Tellimagrandin II has a concentration of more than 30 μg/mL. In another embodiment, the Tellimagrandin II has a concentration of more than 40 μg/mL. In one embodiment, the subject is human.

TABLE 1

The minimum inhibitory concentration of each antibiotic when acts with Tellimagrandin II

| Minimum inhibitory concentration (μg/mL) | | Oxacillin | Erythromycin | Penicillin | Kanamycin | Levofloxacin | Doxycycline | TG II |
|---|---|---|---|---|---|---|---|---|
| MSSA | | 4 | 128 | >512 | >512 | >512 | 128 | 64 |
| MRSA | 19615 | 512 | >512 | >512 | >512 | >512 | >512 | 128 |
| | 18271 | >512 | >512 | >512 | >512 | >512 | >512 | 128 |
| | 18631 | >512 | >512 | >512 | >512 | >512 | 256 | 128 |
| Standard MRSA | | 512 | >512 | >512 | >512 | 32 | 64 | — |

TG II: Tellimagrandin II;
MRSA: Methicillin-resistant *Staphylococcus aureu*
MSSA: Methicillin-susceptible *Staphylococcus aureu*
Unit: μg/mL One MSSA strain, three MRSA strains (19615, 18271, and 18631) and one standard MRSA strain (ATCC 33591) were used. The tested reagents are oxacillin, erythromycin, penicillin, kanamycin, levofloxacin, doxycycline and Tellimagrandin II.

TABLE 2

The synergistic effect of antibiotics and Tellimagrandin II

| Anti-microbial reagent | TG II | Non-drug resistant *Staphylococcus aureus* MIC | FIC | 19615 MIC | FIC | 18271 MIC | FIC | 18631 MIC | FIC |
|---|---|---|---|---|---|---|---|---|---|
| Oxacillin | — | 4 | — | 512 | — | 512 | — | 512 | — |
|  | 30 µg/mL | <2 | 0.5 | <2 | 0.004 | 32 | 0.0063 | 64 | 0.125 |
|  | 40 µg/mL | <2 | 0.5 | 4 | 0.008 | 16 | 0.0031 | 8 | 0.016 |
| Doxycycline | — | 128 | — | 512 | — | 512 | — | 256 | — |
|  | 30 µg/mL | 16 | 0.125 | 16 | 0.031 | 2 | 0.004 | 2 | 0.008 |
|  | 40 µg/mL | 8 | 0.016 | 8 | 0.016 | 2 | 0.004 | 2 | 0.008 |
| Levofloxacin | — | >512 | — | >512 | — | >512 | — | >512 | — |
|  | 30 µg/mL | 8 | 0.016 | 512 | 1 | 512 | 1 | 512 | 1 |
|  | 40 µg/mL |  |  | 512 | 1 | 512 | 1 | 512 | 1 |

TG II: Tellimagrandin II

The antibiotics demonstrated synergistic effect with Tellimagrandin II are oxacillin, doxycycline, and levofloxacin. The minimum inhibitory concentration (MIC) and fractional inhibitory concentration index (FIC) were calculated. The FIC values of synergistic effect, addictive effect, indifference and antagonist effect are <0.5, 0.5~<1, 1~≤4 and 4 respectively.

TABLE 3

The minimum inhibitory concentration of each antibiotic for acting synergistically with Tellimagrandin II

| MIC (µg/ml) | Tellimagrandin II (40 µg/ml) | MSSA MIC | FIC | 19615 MIC | FIC | 18631 MIC | FIC | 18271 MIC | FIC |
|---|---|---|---|---|---|---|---|---|---|
| Oxacillin | − | 4 | — | 512 | — | 512 | — | 512 | — |
|  | + | 2 | 0.5 | 4 | 0.008 | 8 | 0.016 | 16 | 0.031 |
| Ampicillin | − | 512 | — | 512 | — | 512 | — | 512 | — |
|  | + | 256 | 0.50 | 512 | 1.00 | 512 | 1.00 | 16 | 0.031 |
| Levofoxacin | − | 512 | — | 512 | — | 256 | — | 512 | — |
|  | + | 512 | 1.00 | 512 | 1.00 | 512 | 2.00 | 512 | 1.00 |
| Erythromycin | − | 128 | — | 512 | — | 512 | — | 512 | — |
|  | + | 64 | 0.50 | 512 | 1.00 | 512 | 1.00 | 512 | 1.00 |
| Kanamycin | − | 512 | — | 512 | — | 512 | — | 512 | — |
|  | + | 512 | 1.00 | 512 | 1.00 | 512 | 1.00 | 512 | 1.00 |
| Doxycycline | − | 128 | — | 512 | — | 256 | — | 512 | — |
|  | + | 8 | 0.063 | 8 | 0.016 | 2 | 0.008 | 2 | 0.004 |
| Vancomycin | − | >2 | — | 4 | — | 4 | — | 4 | — |
|  | + | >2 | — | 4 | 1.00 | 4 | 1.00 | 4 | 1.00 |

One MSSA strain and three MRSA strains (19615, 18271, and 18631) were used. The tested antibiotics were oxacillin, ampicillin, levofoxacin, erythromycin, kanamycin, doxycycline and vancomycin. The minimum inhibitory concentration (MIC) and fractional inhibitory concentration index (FIC) were calculated. The FIC values of synergistic effect, addictive effect, indifference and antagonist effect are <0.5, 0.5~<1, 1~≤4 and 4 respectively.

TABLE 4

The synergistic effect of oxacillin and Tellimagrandin II against 14 clinical isolated MRSA strains

| Strains | MIC μg/ml | | FIC | outcome |
|---|---|---|---|---|
| | Oxacillin | Oxacillin + TGII | | |
| MRSA 1 | 512 | 4 | 0.008 | Synergy |
| MRSA 2 | 512 | 4 | 0.008 | Synergy |
| MRSA 3 | 512 | 4 | 0.008 | Synergy |
| MRSA 4 | 512 | 2 | 0.004 | Synergy |
| MRSA 5 | 512 | 2 | 0.004 | Synergy |
| MRSA 6 | 256 | 2 | 0.008 | Synergy |
| MRSA 7 | 256 | 2 | 0.008 | Synergy |
| MRSA 8 | 128 | 2 | 0.016 | Synergy |
| MRSA 9 | 128 | 2 | 0.016 | Synergy |
| MRSA 10 | 64 | 2 | 0.031 | Synergy |
| MRSA 11 | 64 | 4 | 0.063 | Synergy |
| MRSA 12 | 64 | 4 | 0.063 | Synergy |
| MRSA 13 | 64 | 2 | 0.031 | Synergy |
| MRSA 14 | 32 | 2 | 0.063 | Synergy |

14 clinical isolated MRSA strains were tested with oxacillin and Tellimagrandin II (40 μg/mL) and the FIC index was calculated. The FIC values of synergistic effect, addictive effect, indifference and antagonist effect are <0.5, 0.5~<1, 1~≤4 and 4 respectively.

In one embodiment, the Tellimagrandin II and polyketide antibiotic act synergistically through an anti-oxidative mechanism.

In one embodiment, the β-lactam antibiotic acts with Tellimagrandin II to reduce Penicillin-binding protein 2a expression in Staphylococcus aureus. In another embodiment, the β-lactam antibiotic acts with the Tellimagrandin II to inhibit mecA gene expression in Staphylococcus aureus.

TABLE 5

The DPPH free-radical scavenging activity of Tellimargrandin II with or without $FeCl_2$; Vitamin C acts as an antioxidant

| $FeCl_2$ ( 50 μM ) | | DPPH free-radical scavenging activity (%) | |
|---|---|---|---|
| | | $+FeCl_2$ | $-FeCl_2$ |
| Tellimagrandin II | 20 μg/mL | 56.61 ± 4.05 | 80.52 ± 0.4 |
| | 40 μg/mL | 57.43 ± 2.49 | 79.47 ± 0.2 |
| Vitamin C | 100 μM | — | 81.09 ± 0.5 |

TABLE 6

The anti-microbial activity of Tellimargrandin II and doxycycline against MRSA in the presence of $FeCl_2$ (50 μM)

| MIC □(μg/mL) | TGII |
|---|---|
| SA | 64 |
| 19615 | 512 |
| 18271 | 512 |
| 18631 | 512 |

The MIC of Tellimagrandin II and doxycycline is higher in the absence of $FeCl_2$ when compared with that in the presence of $FeCl_2$ (Table 6). This suggests that the anti-MRSA activity of Tellimagrandin II and doxycycline is inhibited in the presence of $FeCl_2$.

In one embodiment, the Tellimagrandin II inhibits Staphylococcus aureus biofilm formation.

The present invention also provides a method of anti-inflammation comprising administering an effective amount of Tellimagrandin II, its pharmaceutically acceptable salt, enantiomer, isomer or tautomer to a subject. In one embodiment, the method of anti-inflammation is used to treat sepsis.

In one embodiment, the Tellimagrandin II reduces nitric oxide and prostaglandin $E_2$ production. In another embodiment, the Tellimagrandin II increases heme oxygenase-1 production.

In one embodiment, the Tellimagrandin II has a concentration in the range of 10-50 μM. In another embodiment, the Tellimagrandin II has a concentration in the range of 25-50 μM. In one embodiment, the subject is human.

The present invention further provides a method of treating leukemia comprising administering an effective amount of Tellimagrandin II, its pharmaceutically acceptable salt, enantiomer, isomer or tautomer to a subject.

In one embodiment, the Tellimagrandin II induces cell apoptosis and cell cycle arrest of leukemia cell. In another embodiment, the Tellimagrandin II induces cell apoptosis by increasing intracellular active oxygen species. In still another embodiment, the cell apoptosis of leukemia cell is induced by activating Caspase 3 and Caspase 7. In another embodiment, the cell cycle arrest of leukemia cell is arrested in G2/M phase.

In one embodiment, the Tellimagrandin II has a concentration in the range of 20-80 μM. In another embodiment, the Tellimagrandin II has a concentration in the range of 40-80 μM. In another embodiment, the Tellimagrandin II has a concentration in the range of 50-80 μM. In one embodiment, the subject is human.

The next examples provide some exemplary embodiments of the present invention as follows:

EXAMPLES

The examples below are non-limiting and are merely representative of various aspects and features of the present invention.

Example 1

Cell Viability Assay

Cell viability was measured using alamarBlue. For cell viability assays, human embryonic kidney cell line HEK 293 and human hepatoma cell line Hep G2 were plated 180 μL in each well on a 96-well plate (for HEK 293, at a density of about 10,000 cells/well; for Hep G2, at a density of about 7500 cells/well). The cells were grown overnight (16~18 hours) and left to attach. After overnight incubation, 20 μL of Tellimagrandin II was added to give final concentrations of 0, 20, 30, 40 and 50 μg/mL. The cultures with 0 μg/mL Tellimagrandin II and without adding additional drug (medium only) were as controls. The cells are then incubated in a 5% $CO_2$, 37° C. incubator for 24 hours. After 24 hours, 100 μL of alamarBlue was added to each well, and cultured in a 5% $CO_2$, 37° C. incubator for 4 hours. Absorbance was monitored at 570 nm and 600 nm and cell viability was determined.

Figure 2:
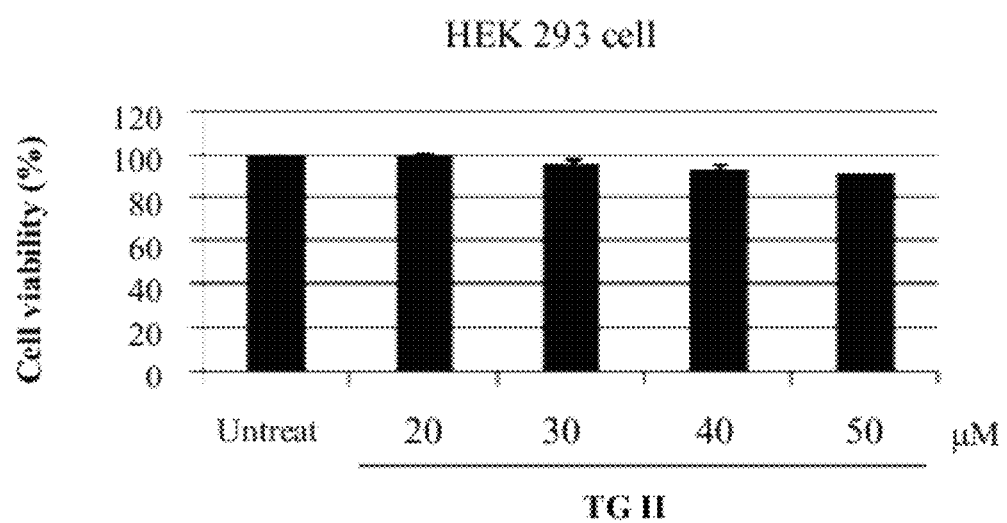
FIG. 2 shows effects of Tellimagrandin II on cell viability in human embryonic kidney cell line HEK 293.

FIG. 2 showed effects of Tellimagrandin II on cell viability in Human embryonic kidney cell line HEK 293. Y-axis represents the percentage of viable cells, x-axis corresponds to the control and concentrations of Tellimagrandin II in 20, 30, 40 and 50 µg/mL.

Figure 3:
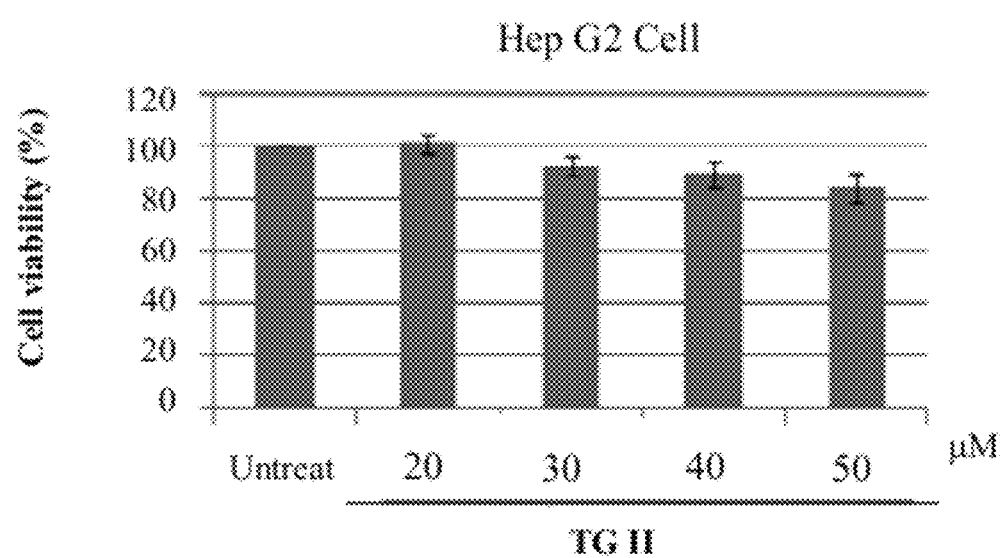
FIG. 3 shows effects of Tellimagrandin II on cell viability in human hepatoma cell line Hep G2.

X-axis corresponds to the control and concentrations of Tellimagrandin II in 20, 30, 40 and 50 µg/mL. Standard deviation was determined as 0, 1.59, 2.01, 1.64 and 0.87, respectively. FIG. 3 showed effects of Tellimagrandin II on cell viability in human hepatoma cell line Hep G2. Y-axis represents the percentage of viable cells, x-axis corresponds to the control and concentrations of Tellimagrandin II in 20, 30, 40 and 50 µg/mL. Standard deviation was determined as 3.480, 3.95, 4.83 and 5.73, respectively. As showed in FIG. 2 and FIG. 3, Tellimagrandin II showed low toxicity in human embryonic kidney cell line and human hepatoma cell line. Cell viability was maintained at least 80% for cells treated with 40 µg/mL Tellimagrandin II.

Minimum Inhibitory Concentration, MIC

A serial of twofold dilution of the tested antibiotics (oxacillin, erythromycin, ampicillin, kanamycin, levofoxacin, vancomycin and doxycycline) was perform by Broth microdilution method to a final concentration of 2-512 µg/mL. The bacterial overnight culture was collected and re-suspended in the Muller-Hilton (M-H) broth. An aliquot of cell suspension ($OD_{600}$=0.1) was prepared. The bacterial suspensions were plated in 96-well plate and incubated with test antibiotics at 37° C. in a 5% $CO_2$ incubator (Table 1 to Table 4).

Fractional Inhibitory Concentration Index (FIC Index)

The synergy, synergy and antagonism between two drugs was evaluated by the following formula:

$$FIC = \frac{MIC \text{ under synergistic effect of } TG \text{ II and the antibiotic}}{MIC \text{ under the antibiotic}}$$

The criteria of fractional inhibitory concentration index:

| Index | FIC |
|---|---|
| synergy | <0.5 |
| synergy | 0.5-4 |
| antagonism | >4 |

As shown in Table 1 to Table 4, Tellimagrandin II and oxacillin or doxycycline were defined as synergy, their FIC indexes lower than 0.5.

1,1-diphenyl-2-picrylhydrazyl (DPPH) Scavenging Assay

Test reagents, natural extracts and Vitamin C (ascorbic acid) were dissolved in methanol to make a stock solution 10×. Vitamin C was used as the positive control. 120 µM DPPH solution was prepared. Taken 20 µL of stock reagents, natural extracts and Vitamin C on a 96-well microplate, and methanol was added to make up to the total volume of 100 µL. Control was 100 µL methanol. Each sample was mixed with 100 µL DPPH solution and incubated in the dark for 40 minutes. DPPH level of each well was evaluated by detecting the optical density of each well at 517 nm and the results were shown in Table 5.

Time-Killing Curve

Figure 4:
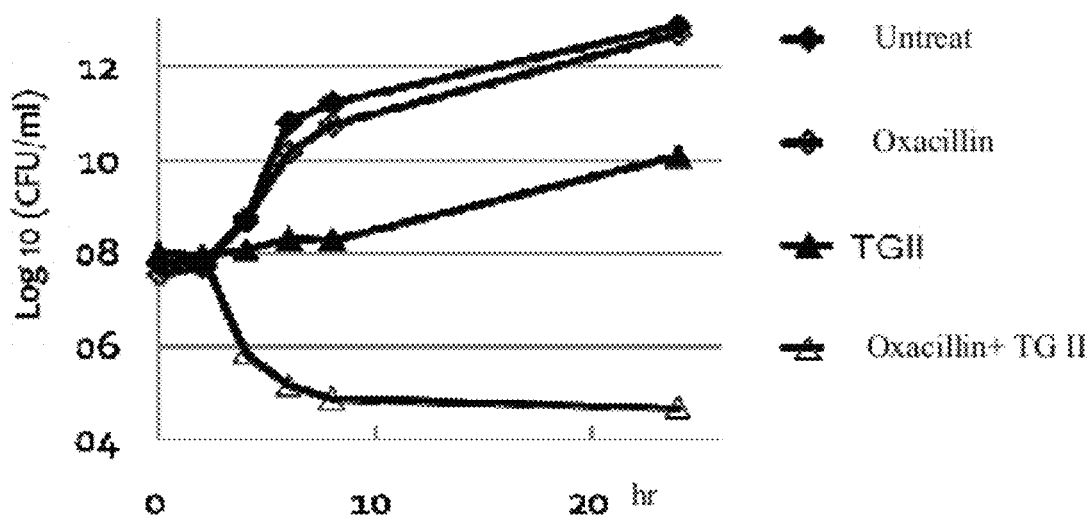
FIG. 4 shows the combination of Oxacillin plus Tellimagrandin II for synergistic antimicrobial activity against bacteria. Y-axis: mean colony counts ($Log_{10}$ cfu/mL), X-axis: culture time. There are four groups: ◆, control group, without adding any drug; ◇, test group with 5 μg/mL Oxacillin; ▲, test group with 40 μg/mL Tellimagrandin II; Δ, test group with 40 μg/mL Tellimagrandin II and 5 μg/mL Oxacillin.
Figure 5:
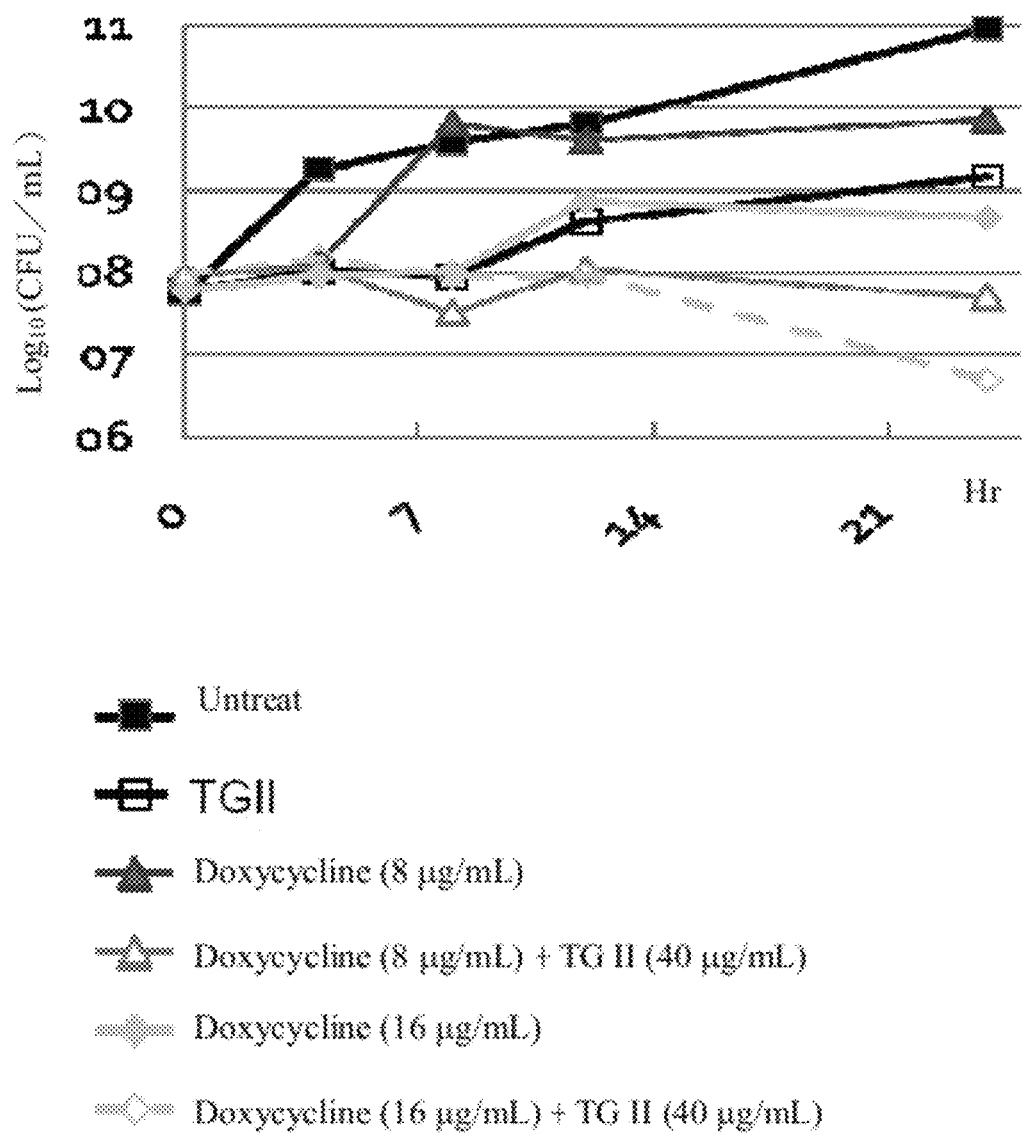
FIG. 5 shows the combination of Doxycyxline plus Tellimagrandin II for synergistic antimicrobial activity against bacteria. Y-axis: mean colony counts ($Log_{10}$ cfu/mL), X-axis: culture time. There are six groups: ■, control group, without adding any drug; □, test group with 40 μg/mL Tellimagrandin I; ▲, test group with 8 μg/mL Doxycycline; Δ, test group with 8 μg/mL Doxycycline and 40 μg/mL Tellimagrandin II; ◆, test group with 16 μg/mL Doxycycline; ◇, test group with 16 μg/mL Doxycycline and 40 μg/mL Tellimagrandin II.

MRSA 19615 bacteria were cultured overnight, collected and re-suspended in 25 mL MHB containing TGII and antibiotics of the indicated final concentration. To dilute the samples, samples were taken from the suspension at indicated time interval and mixed with filtered PBS, followed by spreading the diluted sample on MHA plated for two plates/each time point. Colony counts between 150 and 500 colonies in first time point was used to determine the dilution fold. Time-killing curves were calculated from colony counting and data analyzing was performed after overnight culture. Bacterial time-kill curves were constructed by plotting mean colony counts ($log_{10}$ cfu/mL) versus time (FIGS. 4 and 5). As FIG. 4 showed, oxacillin (5 µg/mL) treatment alone failed to inhibit bacterial growth. Oxacillin (5 µg/mL) and Tellimagrandin II (40 µg/mL) used together which inhibited the visible growth of bacteria after 24 hours. As FIG. 5 showed, synergistic effects were observed for the Tellimagrandin II/doxycycline combinations (40 µg/mL Tellimagrandin II and 8 µg/mL doxycycline; 40 µg/mL Tellimagrandin II and 16 µg/mL doxycycline). Hence, bactericidal efficiency of the 40 µg/mL Tellimagrandin II and 16 µg/mL doxycycline combination was much more potent.

Western Blotting Analysis

Figure 6:
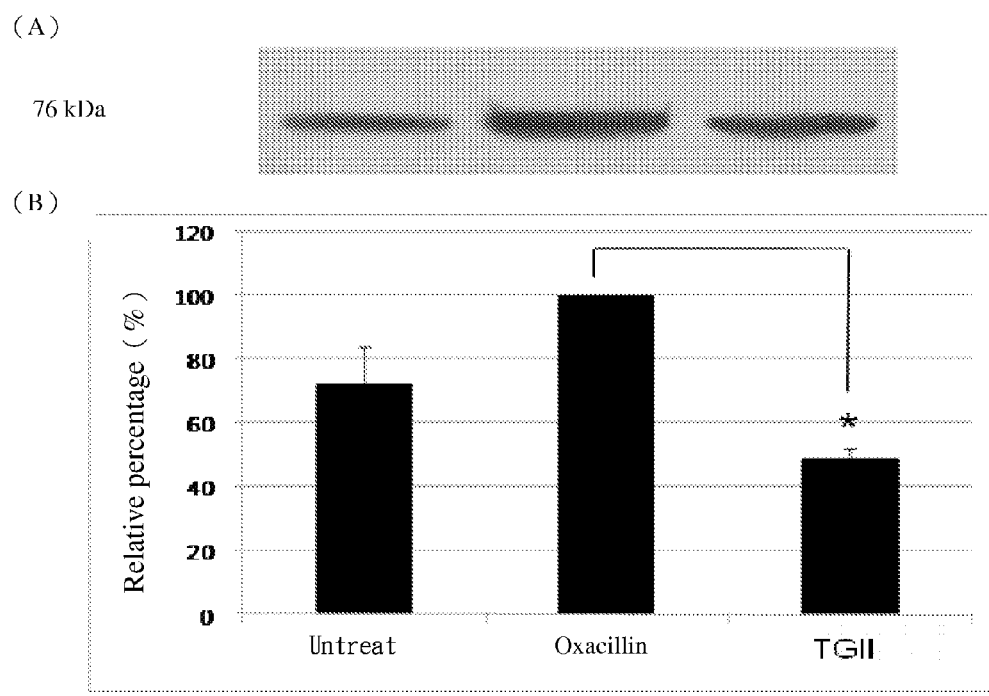
FIG. 6 shows effects of Tellimagrandin II on expression of penicillin-binding protein 2a (PBP2a) (N=3). PBP2a expression: (A) Western blotting analysis result (B) Quantitative analysis of western blot of PBP2a protein from FIG. 6(A). Intensity of each protein band was quantitated using the AlphaEase FC software, and the test group with 2 μg/mL Oxacillin set as 100%. The first bar represents the control group, the second bar represents the test group with 2 μg/mL Oxacillin and the third bar represents the test group with 40 μg/mL Tellimagrandin II. The standard deviation (SD) from left to right are: 11.77, 0 and 2.5; *p<0.01.

Protein samples (15 µg) were mixed with 5× Sample buffer and boiled in 1× Sample buffer for 5 min and then cooled quickly that proteins be denatured to their constituent polypeptide chains. Equal amounts of protein (15 µg) were separated on 10% SDS-PAGE at 17 mA for 2 hours, and transferred to PVDF membrane using wet transfer procedure. The PVDF membrane was blocked for half hour at room temperature in t-BST buffer containing 5% (w/v) non-fat dry milk to prevent nonspecific binding then probed with primary antibodies (Rabbit-anti-penicillin binding protein, dilution 1:5000) in 5% non-fat dry milk for 16~18 hours at 4° C. Anti-Groel was used as internal controls (dilution 1:80,000; purchased from Sigma). After washing with t-BST three times for 5 minutes each, the membrane was incubated for half hour at room temperature with horseradish peroxidase (HRP)-conjugated secondary antibodies in 5% (w/v) non-fat dry milk. The membrane was washed three times for 5 minutes each, followed by using an enhanced chemiluminescence system and exposed to film. The quantification results of Western blot were showed in FIG. 6. As showed in FIG. 6, 40 µg/mL of Tellimagrandin II alone could inhibit the expression of the penicillin-binding protein 2a (PBP2a) in bacteria.

RNA Isolation and Quantification

The RNA isolation procedure was performed by Roche High Pure RNA Isolation Kit. In brief, each treated bacterial sample was collected by centrifugation at 13,000 rpm for 2 minutes and lysed by 20 µM lysostaphin treatment at 37° C. for 15 minutes. The samples were loaded into high pure filter tubes after adding with 400 µL lysis-binding buffer-mixed sample and then centrifuged at 9,600 g for 1 minute. The flow through were removed and the filter tubes were put into the collection tubes. 90 µL of pre-mixed DNase incubation buffer and 10 µL of DNase I were added to the filter tubes, which followed by 1 hour reaction. The wash buffer I, II and III were added to the filter tubes serially and the flow through were removed by centrifugation (9,600 g for 1 minute) between each step. The final RNA products were eluted by 30 µL elute buffer and collected into a clean eppendrof.

The RNA preparations were quantified using a Backman DU800. Two microliters (2 µL) of RNA sample added with 98 µL of elute buffer in a PCR tube and mixed well. The concentration and purity of the RNA samples were assessed using the Backman DU800 spectrophotometer (the dilution factor is 50).

Reverse Transcription PCR

SuperScript III Reverse Transcriptase (Invitrogen) was used in this study. Two micrograms (2 µg) of the purified RNA was mixed with 1 μL of Oilgo dT, 1 μL of random primer (250 ng) and 1 μL of 10 mM dNTP Mix (dATP, dGTP, dCTP and dTTP, 10 mM each) in a PCR reaction tube. Heated the mixture to 65° C. for 5 min and quick chilled on ice. Four microliters (4 μL) of 5× Fist-stand buffer, 1 μL of DTT (0.1 M) and 0.5 μL of SuperScript III RTase were added and mixed well. The mixture was incubated at 25° C. for 5 minutes, 55° C. for 60 minutes, and 70° C. for 5 minutes.

Real-Time PCR

Figure 7:
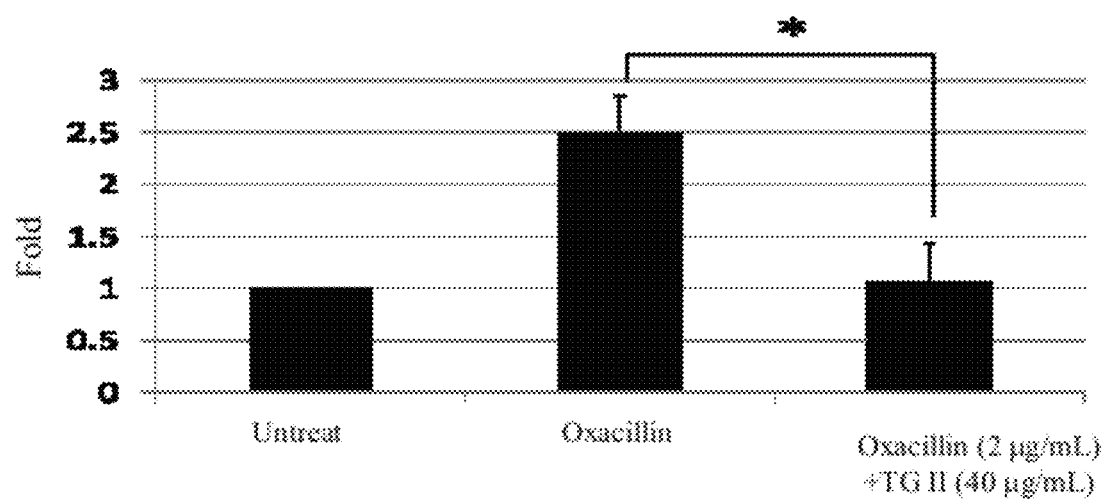
FIG. 7 shows effects of Tellimagrandin II on expression of mecA gene (N=3, *p<0.05).

Roche LightCycler system was used to perform RT-PCR in order to study the expression of target gene. Two micrograms (2 μg) of the cDNA was mixed with 4 μM $MgCl_2$, 5 μM primers and 2 μL of 10× LightCycler FastStart DNA Master SYBR Green I mixture (Roche) in a reaction plate and mixed well. Amplification conditions were as follows: denaturation for 1 cycle at 95° C. for 0.5 minute, 95° C. for 15 seconds, 60° C. for 30 seconds and 72° C. for 30 seconds. After PCR run, an additional melt analysis was performed (from 60° C. to 95° C. with a temperature transition rate of 0.1° C./s); this verified the specificity of the amplification reaction. The fold change of RNA gene expression was calculated by the equation $2^{-\Delta\Delta Ct}$, where Ct is the cycle threshold. The cycle threshold (Ct) is defined as the number of cycles required for the fluorescent signal to cross the threshold in RT-PCR. ΔCt was calculated by subtracting the Ct values of the endogenous control from the Ct values of the target gene. ΔΔCt was then calculated by subtracting ΔCt of the control from ΔCt of sample. As shown in FIG. 7, the first bar represents the control group, the second bar represents the test group with 2 μg/mL Oxacillin and the third bar represents the test group with 40 μg/mL Tellimagrandin II and 2 μg/mL of Oxacillin. The standard deviation (SD) from left to right are: 0, 0.37 and 0.37; *p<0.05. The result showed in FIG. 7, 2 mg/mL of Oxacillin and 40 μg/mL Tellimagrandin II combination inhibited mecA gene expression.

```
             Primer sequences:

ftsZ gene ftsZ forward primer       TTACTGGTGGCGAGTCATTG
   (SEQ ID NO: 1)
   ftsZ reverse primer       TTTACGCTTGTTCCGAATCC
   (SEQ ID NO: 2)

mecA gene mecA forward primer       CTGCTATCCACCCTCAAACAG
   (SEQ ID NO: 3)
   mecA reverse primer       TCTTCGTTACTCATGCCATACA
   (SEQ ID NO: 4)
```

Transmission Electron Microscopy (TEM)

Figure 8:
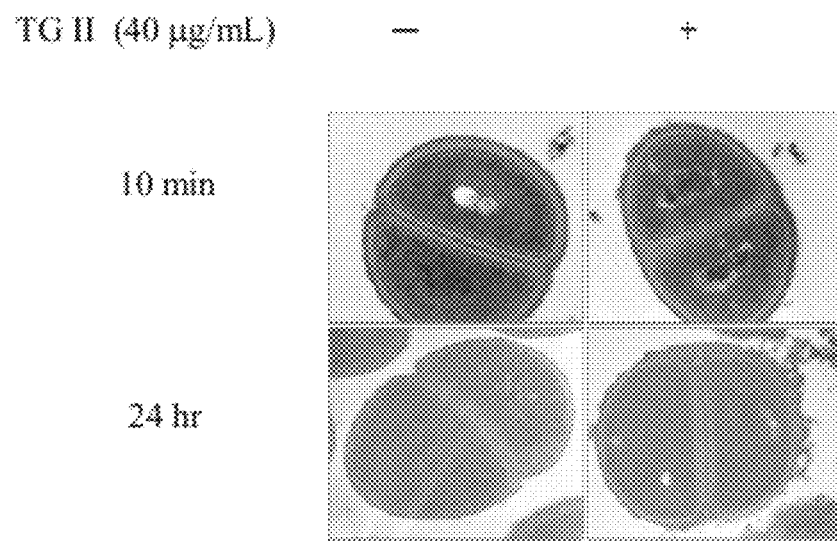
FIG. 8 shows the phenotypic changes observed from the scanning electron microscopy (SEM).

Before observed by TEM, the bacteria were cultured overnight on plate, collected and suspended in either 10 mL MHB or 10 mL MHB containing 40 μg/mL Tellimagrandin II. The bacterial solution were diluted to an optical density at 600 nm ($OD_{600}$) of 0.1, and cultured for 10 minutes or 24 hours. Then, the cells were centrifuged at 10,000 rpm/min and suspended in the fixing fluid, the fixed time can not exceed 24 hours. The sample for TEM was sent to departments of Laboratory Medicine and Clinical Research, Kaohsiung Medical University Hospital (Kaohsiung, Taiwan, ROC). As shown in FIG. 8, the bacteria sample which treated with 40 μg/mL Tellimagrandin II and cultured for 10 minutes showed unsmooth tooth surfaces compared with control group. The phenotype showed a significant correlation in the bacteria sample which treated with 40 μg/mL Tellimagrandin II and cultured for 24 hours.

Biofilm Formation

Bacteria was grown overnight (16~18 hours) on agar plate. Then, collected and re-suspended in 0.45% sterile PBS and diluted in sterile PBS to final optical density at 600 nm ($OD_{600}$) of 0.1. Polystyrene 96-well microtitre plates were filled with 150 μL of culture medium and 20 μL of bacterial solution per well. The cultures were allowed to stand at 37° C. for 18 hours. After the incubation period, cultures were removed, and microtitre plate wells were gently washed three times with 300 μL of sterile PBS to remove loosely associated bacteria, then dried at 60° C. oven for 1 hour. Samples were stained by the addition of the 2% dye solution (150 μL) to each well above the initial inoculation level and incubated for 15 minutes. The plate was then washed in fresh water. The intensity of staining was measured after the addition of 95% alcohol (150 μL) to each dry well. The samples were incubated at room temperature for 30 min, after which the $OD_{517}$ values were measured on a plate reader.

TABLE 7

Effect of Tellimagrandin II on bacterial biofilm formation.

Without adding with Tellimagrandin II

| | Absorbance | | | | | | |
|---|---|---|---|---|---|---|---|
| Group | 1 | 2 | 3 | 4 | Average OD value | Standard deviation | Cut-off value |
| Strain | 0.382 | 0.651 | 0.298 | 0.288 | 0.405 | 0.169 | 0.087 |
| Negative control | 0.065 | 0.076 | 0.068 | NA | 0.070 | 0.006 | |

| Cut-off value | 2 × ODc | 4 × ODc |
|---|---|---|
| 0.087 | 0.173 | 0.347 |
| OD (average OD value of the strain − ODc = 0.405 − 0.087) | | 0.318 |

With adding with 40 μg/mL Tellimagrandin II

| | Absorbance | | | | | | |
|---|---|---|---|---|---|---|---|
| Group | 1 | 2 | 3 | 4 | Average OD value | Standard deviation | Cut-off value |
| Strain | 0.153 | 0.259 | 0.167 | 0.246 | 0.206 | 0.054 | 0.167 |
| Negative control | 0.099 | 0.115 | 0.067 | NA | 0.094 | 0.024 | |

| Cut-off value | 2 × ODc | 4 × ODc |
|---|---|---|
| 0.167 | 0.334 | 0.668 |
| OD (average OD value of the strain − ODc = 0.206 − 0.167) | | 0.039 |

Optical density cut-off value (ODc)=average OD of negative control+3× standard deviation (SD) of negative control (The interpretation of biofilm production was done according to the criteria of Srdjan et al. (APMIS 115: 891-9, 2007). MRSA 17199 were used as control strain.

Interpretation of biofilm production:

| Average OD value | Biofilm production |
|---|---|
| OD ≤ ODc | Non |
| ODc < OD ≤ 2 × ODc | Weak |

-continued

| Average OD value | Biofilm production |
|---|---|
| 2 × ODc < OD ≤ 4 × ODc | Moderate |
| 4 × ODc < OD | Strong |

Example 2

The mouse macrophage cell line RAW264.7. used in the following studies.
Cell Viability Assay
AlamarBlue reagent was used to assess cell viability. RAW264.7 cells ($2 \times 10^4$ in 200 μL of medium) were seeded on the 96-well plate. After overnight incubation, cells were serum starved in DMEM medium containing 2% Fetal Bovine Serum (FBS) for 3 hours. There were several groups: cells without DMSO or Tellimagrandin II treatment (controls); cell treated with DMSO (control); cells treated with Tellimagrandin II with different concentrations (10, 25, 50, 75 and 100 μM, diluted in DMSO) (test groups). Each group was determined in duplicate.

After 24 hours, the cell medium was removed and discarded, and the cells were resuspended with 180 μL of fresh culture medium. Each cell suspension was added with 20 μL alamarBlue. The plate was then placed in incubator for another 4 hours. After incubation, the absorbance of the medium was measured at 570 and 600 nm, and cell viability was analyzed by using the following formula:

$$\frac{(O2 \times A1) - (O1 \times A2) \times 100}{(O2 \times P1) - (O1 \times P2)}$$

Figure 9:
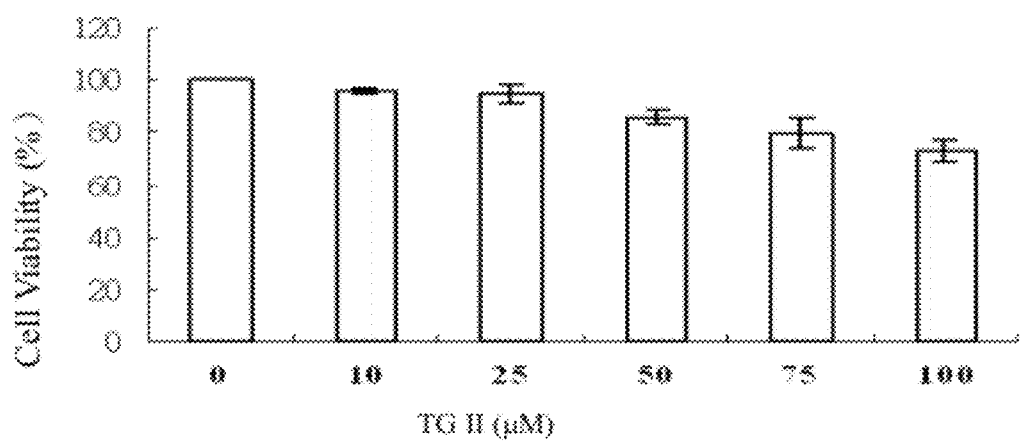
FIG. 9 shows effects of Tellimagrandin II on cell toxicity in mouse macrophage cell line RAW264.7 (N=3, Mean±SD).
Figure 10:
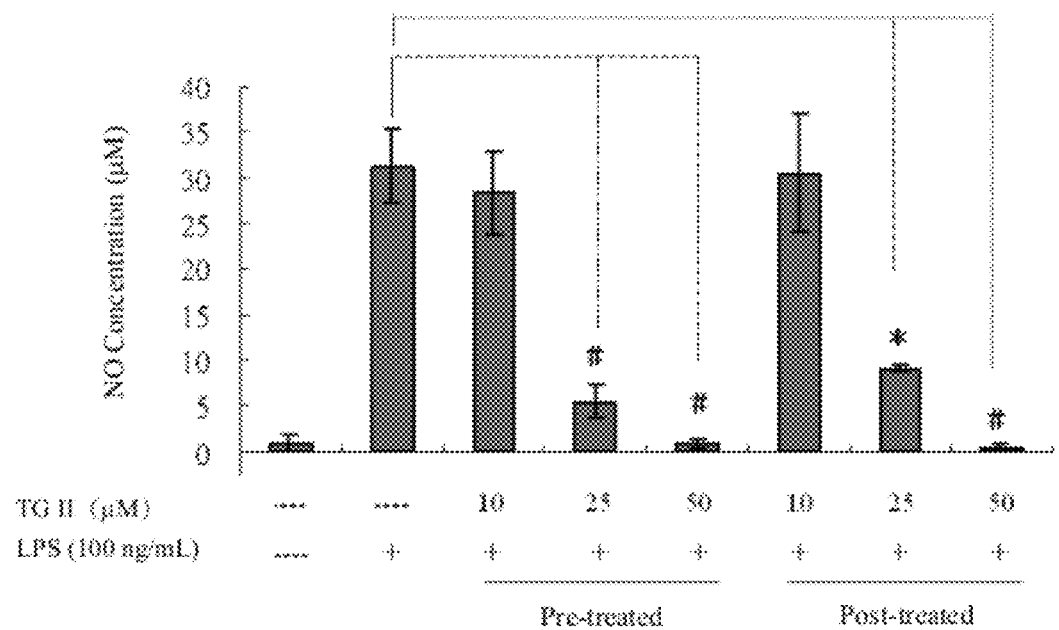
FIG. 10 shows effects of Tellimagrandin II on production of NO which induced by lipopolysaccharide (LPS) (N=3, Mean±SD).
Figure 11:
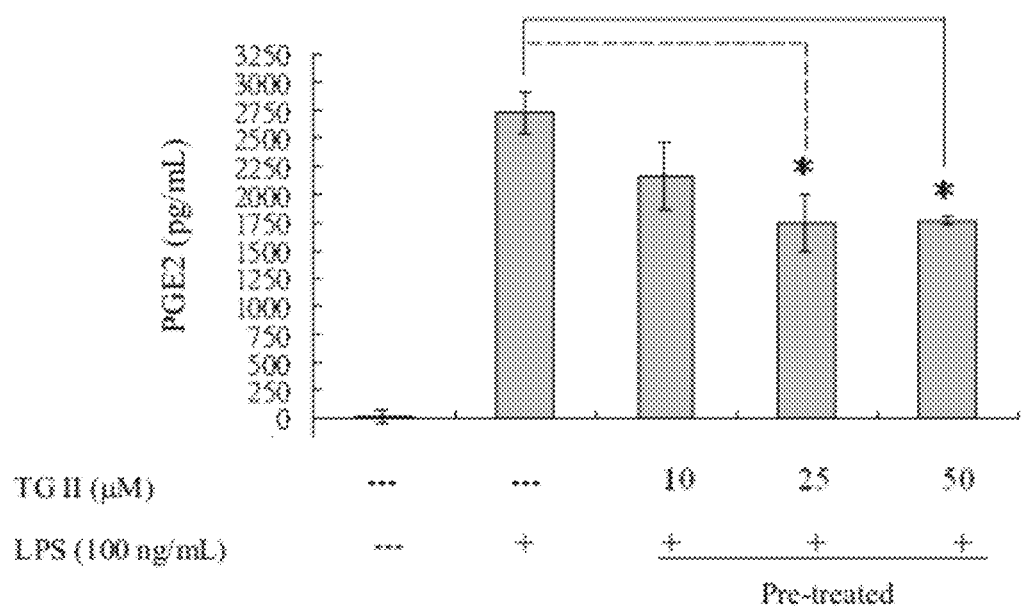
FIG. 11 shows effects of Tellimagrandin II on expression of prostaglandin $E_2$ ($PGE_2$) which induced by lipopolysaccharide (LPS) (N=3, Mean±SD, *p<0.05).
Figure 12:
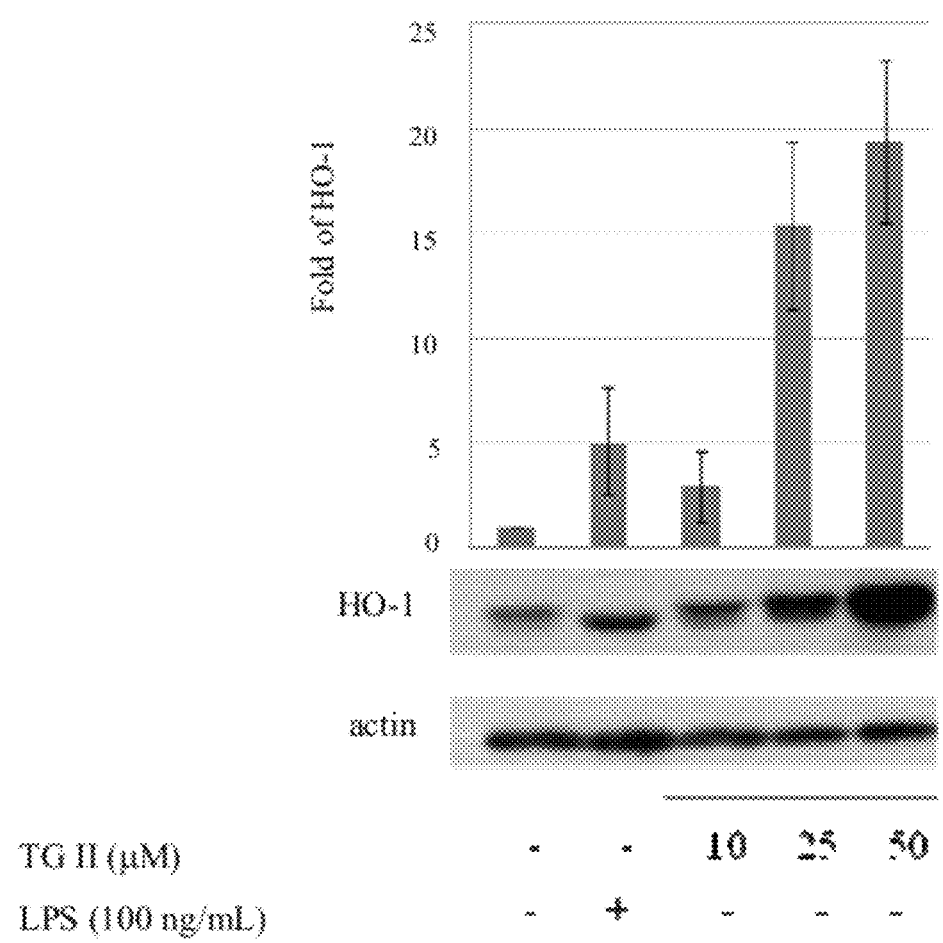
FIG. 12 shows effects of Tellimagrandin II on expression of Heme oxygenase-1 (HO-1) which induced by lipopolysaccharide (LPS) (N=3, Mean±SD).

O1: molar extinction coefficient (E) of oxidized alamarBlue at 570 nm
O2: molar extinction coefficient (E) of oxidized alamarBlue at 600 nm
A1: absorbance of test wells at 570 nm
A2: absorbance of test wells at 600 nm
P1: absorbance of positive growth control well at 570 nm
P2: absorbance of positive growth control well at 600 nm In FIG. 9, the x-axis represents the concentration of Tellimagrandin II, and y-axis represents the cell viability. Results in FIG. 9 showed that the cell viability was not affected significant when treated with Tellimagrandin II at a concentration of 50 μg/mL or lower doses.
NO Production Analysis
Murine macrophage cells were plated in each well on a 12-well plate at a density of about $4 \times 10^5$ RAW264.7 cells/mL. After overnight incubation, cells were serum starved in DMEM medium containing 2% Fetal Bovine Serum (FBS) for 3 hours. Cells stimulated with Lipopolysaccharide (LPS) for 24 hours significantly increased the nitrite levels in the culture media. Endogenous NO production, induced by LPS. Cells were treated with Tellimagrandin II at various concentrations (10, 25 and 50 μM) before and after being treated with LPS. For NO production analysis, culture supernatants were brought to 96-well plate and mixed with Griess reagent. Plates were incubated and then the absorbance was measured at 520 nm. Sodium nitrite ($NaNO_2$) solution (0 M~0.1 M, 8 points) prepared in DMEM was used to generate a standard curve. The nitrite concentrations of samples were determined by interpolation from the standard curve. As shown in FIG. 10, introduction of Tellimagrandin II (either before or after being treated with LPS) decreased the production of LPS-induced NO. The Tellimagrandin II concentrations of the test groups (25 and 50 μM) showed statistically significant. FIG. 10 is framed by a an x-axis labeled the relative order in LPS or Tellimagrandin II treatment and concentrations, and y-axis labeled NO concentration. The control (LPS only) and test groups were compared using a t-test, *p<0.05 (significant) and #p<0.01 (highly significant).
Prostaglandin $E_2$ ($PGE_2$) Assay
One milliliter (1 mL) of murine macrophage cell line RAW264.7 ($4 \times 10^5$ cells/mL) was seeded on a 12-well plate overnight. After overnight incubation, cells were serum starved in DMEM medium containing 2% Fetal Bovine Serum (FBS) for 3 hours. Then, Tellimagrandin II was added so that final concentrations of 10, 25 and 50 μM were obtained. Thus, after a 30-min incubation, murine macrophage cells were treated with LPS for 16 h and the cell culture supernatant was collected. Cell-free supernatants were diluted and PGE 2 in culture supernatants were detected by using a PGE2 assay kit (R&D system). The purpose of the study was to evaluate the LPS-induced PGE2 expression by co-treating with Tellimagrandin II. As showed in FIG. 11, 25 or 50 μM of Tellimagrandin II was added in the cells 30 minutes before being treated with LPS, significantly reduced the expression of PGE2 (the experimental results were compared with the LPS group, P values less than 0.05 were taken as significant).
Western Blot Analysis of Heme Oxygenase-1 (HO-1)
The murine macrophage RAW264.7 cells were plated in 6 cm cell dishes at a seeding density of $5 \times 10^6$ cells/mL and incubated overnight. After overnight incubation, cells were treated with different concentrations of Tellimagrandin II (10, 25 and 50 μM) and LPS and incubated for 24 hours. Cells were washed twice with PBS, scraped and lysed on ice in RIPA buffer, and proteins were obtained. Heme oxygenase-1 expression was analyzed by Western blotting of the whole cell lysates. The results for Western blot data and quantitative analysis showed in FIG. 12. In FIG. 12, the first bar represents the control group, the second bar represents the test group with LPS only and the third, the fourth and fifth bars represent the test groups with 10, 25 and 50 μg/mL Tellimagrandin II (N=3, Mean±SD). As showed in FIG. 12, the expression of Heme oxygenase-1 slightly increased on LPS stimulated cells. Upon Tellimagrandin II treatment (25 or 50 μM) significant increases in Heme oxygenase-1 expression was observed.

Example 3

Cell Viability Assay

Quantitative cell viability assessed using WST-1 assay. WST-1 is a reagent which produces a highly water soluble formazan upon metabolically active cells, allowing a direct colorimetric measurement of cell viability.

The K-562 cells were plated in a 96-well culture plate at a seeding density of 6,000 cells/well (100 μL) and incubated at 37° C. with 5% $CO_2$ for 16~18 hours. Cells were treated with 20 μL Tellimagrandin II to make the final concentrations of 0, 20, 40, 60 and 80 μM, and incubated at 37° C. with 5% $CO_2$ for 24 and 48 hours. Cells without Tellimagrandin II treatment used as a control. Added 12 μL of WST-1 reagent (10:1) to each well of the plate and mixed well, then incubated at 37° C. in a 5% $CO_2$ incubator for 2 hours. After incubation, the absorbance at 450 nm (test wavelength) and 630 nm (reference wavelength) were measured. Data was calculated by subtracting the 630 nm background absorbance from the 450 nm measurement.

Figure 13:
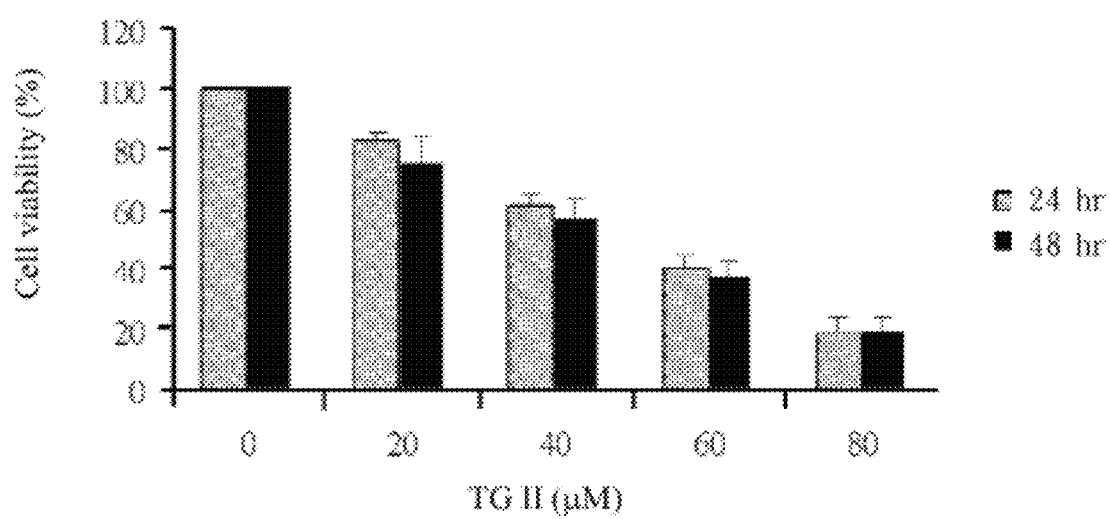
FIG. 13 shows the quantitative cell viability results measured using the WST-1 assay. The cell viability of human erythromyeloblastoid leukemia K-562 cell treated or not with Tellimagrandin II was determined using the WST-1 assay (N=3, Mean±SD, #p<0.01).

The results showed in FIG. 13, the cell viability of K-562 cell treated with Tellimagrandin II at different concentrations for 24 or 48 hours was measured using the WST-1 assay. Cell survival was expressed as percentage of viable cells in the presence with respect to control cultures grown (100%). $IC_{50}$ values were extrapolated from the curves. The value of $IC_{50}$ of 24 hr-test group was 57.01 μM, and the value of $IC_{50}$ of 48 hr-test group was 48.11 μM. The follow-up experiments used Tellimagrandin II at concentrations of 40 μM or 50 μM was based on the results (N=3, Mean±SD, *p<0.05).

FIG. 13 showed the quantitative cell viability results measured using the WST-1 assay. The cell viability of human erythromyeloblastoid leukemia K-562 cell treated or not with Tellimagrandin II was determined using the WST-1 assay (N=3, Mean±SD, #p<0.01).

Cell Cycle Analyses

K-562 cells were plated in 15 cm dish at a density of $5\times10^5$ cells/mL (15 mL) and incubated at 37° C. with 5% $CO_2$ for 16~18 hours. Cells were collected and centrifuged at 700 rpm for 3 minutes at room temperature, and resuspended in culture medium containing 0.04% fetal bovine serum and 8 mM L-glutamine. Then, cells were incubated at 37° C. with 5% $CO_2$ for 16~18 hours.

Collected above cells and plated in 3 cm dishes at an initial density of $5\times10^5$ cells/mL (3 mL). Cells were treated with Tellimagrandin II to final concentrations of 0, 10, 20, 30, 40 and 50 μM, and then incubated at 37° C. with 5% $CO_2$ for 12 and 24 hours.

Figure 14:
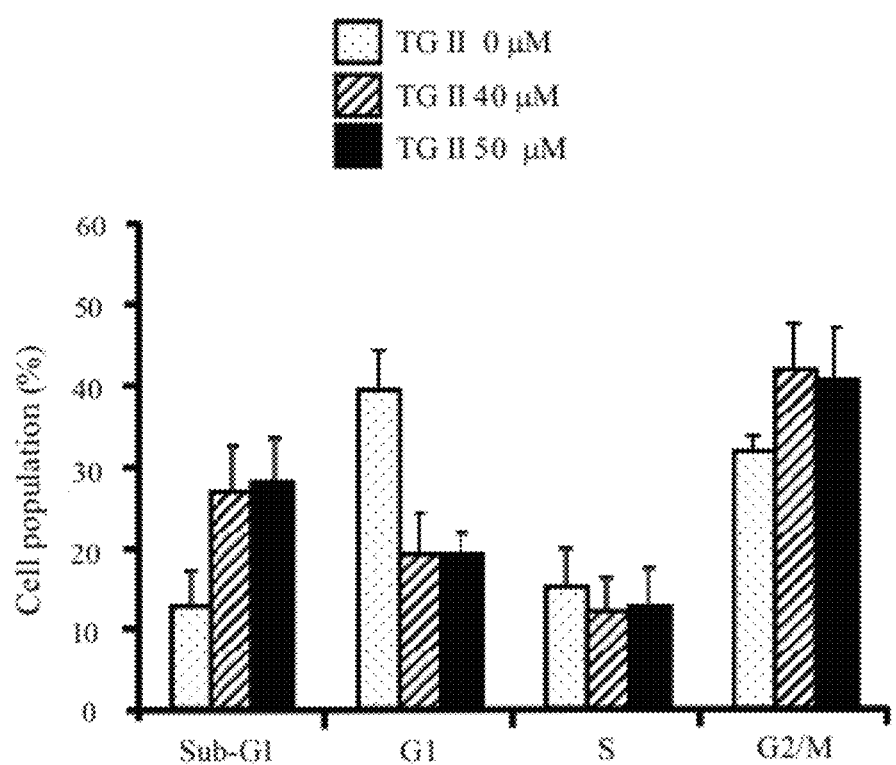
FIG. 14 shows the cell cycle distribution by using flow cytometry. The cell cycle study of human erythromyeloblastoid leukemia K-562 cell treated or not for 24 hours with Tellimagrandin II was determined using flow cytometry (N=3, Mean±SD, *p<0.05).

Cells were centrifuged at a speed of 700 rpm for 5 min at 4° C. and washed once with PBS. Cells were fixed by drop-wise addition of 70% ethanol into the cell suspension. After 16~18 hours, the ethanol-suspended cells were centrifuged at a speed of 35,00 rpm/min for 5 minutes at 4° C. and the ethanol decanted thoroughly. Cells were resuspended in PBS containing RNase A (10 μg/mL) and 1% Triton X-100 and incubated at 37° C. in a 5% $CO_2$ incubator for 30 minutes to 1 hour. For propidium iodide (PI) staining, cells were centrifuged at 3,500 rpm for 5 minutes at room temperature and resuspended in 600 μL PBS. 25 μL of PI (20 μg/mL) solution was added to the mixture and incubated at room temperature in the dark for 1 hour. DNA content analysis of the propidium iodide-stained cells was carried out in a flow cytometer. Cell-cycle analysis by flow cytometry as showed in FIG. 14. The results showed that the percentage of the sub-G1 and G2/M-phase cells increased in Tellimagrandin II treatments dose-dependently (N=3, Mean±SD, *p<0.05).

Apoptosis Detection Test

TUNEL test was used to detect any DNA fragmentation to determine if cell enters apoptosis process.

A total of 10 mL cell solution at the concentration of $1\times10^6$ K-562 cells per mL was cultured with 10 cm cell culture dishes in an incubator supplied with 5% $CO_2$ at 37° C. for 30 minutes so that cells could adapt to the environment. Tellimagrandin II solutions of different concentrations were added by order so that the final concentrations are 0, 10, 20, 30, 40 and 50 μM respectively. The solution was placed in incubator with 5% $CO_2$ at 37° C. for 48 hours before being centrifuged at 3,500 rpm at 4° C. for 5 minutes. After removing the supernatant, the cells were rinsed by PBS once. A total of 1 mL 1% Trioxane (diluted from 10% Trioxane solution with PBS) was added and the solution was left to react at room temperature for 30 minutes to one hour. Then, the solution was centrifuged at 3,500 rpm at 4° C. for 5 minutes. After removing the supernatant, 70% ethanol was added and the solution was placed at −20° C. for 16-18 hours for cell fixation.

Figure 15:
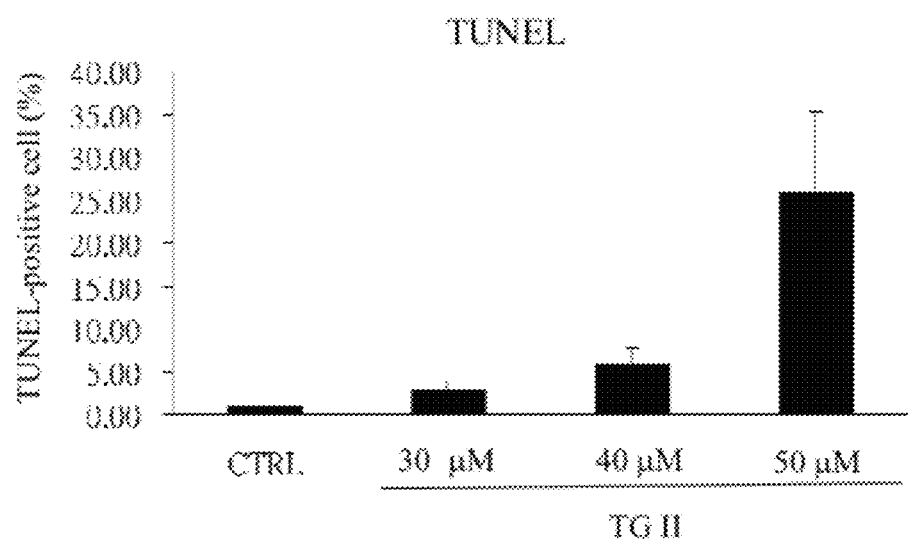
FIG. 15 shows the amount of DNA fragmentation in human erythromyeloblastoid leukemia K-562 cells treated 48 hours with Tellimagrandin II compared to untreated cells (N=3, Mean±SD, *p<0.05).

After cell fixation, the solution was centrifuged at 400 rpm at 4° C. for 10 minutes before removing the supernatant. TUNEL buffer solution 80 μL was added and the solution was left to react at room temperature for 5 minutes. Then EDTA 1 mL was added into the solution, which was then gently mixed. The solution was centrifuged at 3,500 rpm at 4° C. for 5 minutes before removing the supernatant. Then, 50 μL of fluorescent detection reagent for TUNEL test was added into the solution, before which was properly mixed and darkly incubated at 37° C. for an hour. It was centrifuged at 3,500 rpm at 4° C. for 5 minutes and PBS was used to rinse the cells once. Finally, 1 mL PBS was used to resuspend the cells before BD FACS can was used to detect the fluorescent signal and the quantitative results are in FIG. 15. From the quantitative chart for TUNEL test (FIG. 15), we know that fluorescent signals were detected 48 hours after K-562 cells reacted with 30 μM Tellimagrandin II. Furthermore, the variation in signal change was more significant when the concentration was increased to 50 μM (N=3, Mean±SD, *p<0.05).

DNA Ladder Test

K-562 cells treated with Tellimagrandin II were collected for electrophoresis to identify any DNA fragmentation.

A total of 3 mL cell solution at the concentration of $1\times10^6$ K-562 cells per mL was cultured with 6 cm cell culture plates in an incubator supplied with 5% $CO_2$ at 37° C. for 30 minutes so that cells could adapt to the environment. Tellimagrandin II solutions of different concentrations were added by order so that the final concentrations are 0, 20, 30, 40, 50 and 60 μM respectively. The solution was placed in incubator with 5% $CO_2$ at 37° C. for 48 hours before being centrifuged at 2,500 rpm at 4° C. for 5 minutes. After removing the supernatant, it's rinsed by PBS once. Then, cell lysis buffer 100 μL (1% NP-40 dissolved in 20 μM EDTA and 50 μM Tris-HCl, pH 8.0) was added and the solution was shaken at high speed for 10 seconds.

Figure 16:
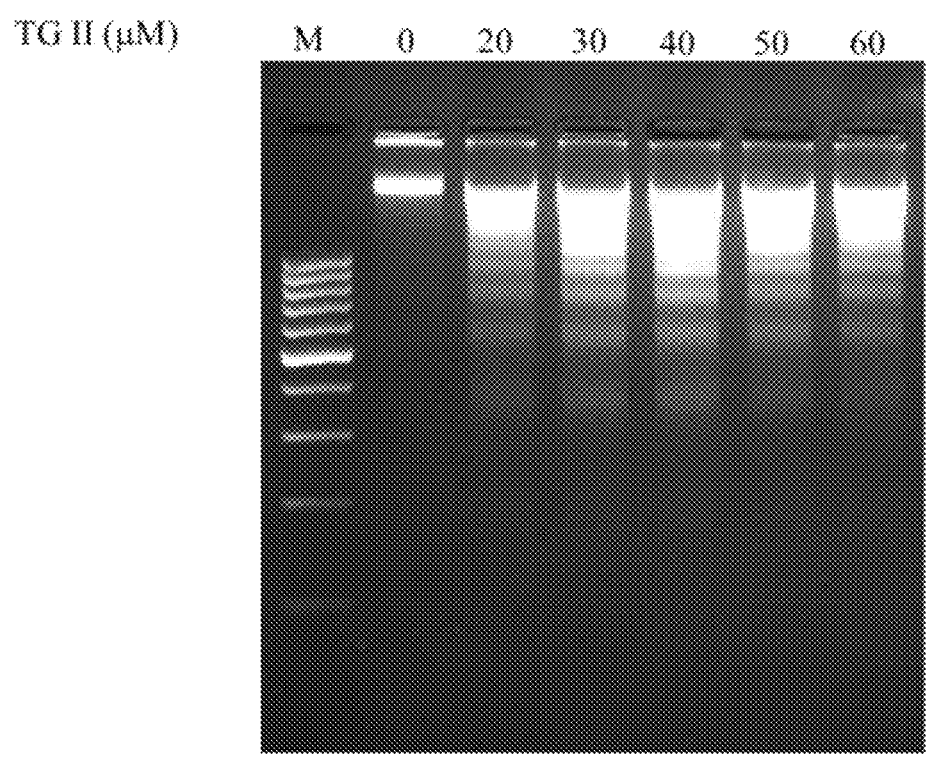

The solution was centrifuged at 3,500 rpm for 5 minutes before 90 μL supernatant was collected and mixed properly with SDS solution 10 μL. RNase A (4 mg/mL) 50 μL was added into the mixed solution then placed in water bath at 56° C. for one hour to remove RNA. Proteinase K (10 mg/mL) 30 μL was then added before another one hour in the water bath at 56° C. to remove protein. 10 M Ammonium acetate of half the total solution volume (90 μL) was added and mixed properly before anhydrous ethanol of twice the total volume (540 μL) was added and mixed properly. The solution was placed under −80° C. for DNA precipitation. The solution was centrifuged at 12,000 rpm at a low temperature for 30 minutes before carefully removing the supernatant to avoid the loss of DNA precipitation. DNA precipitation was rinsed by 70% ethanol 200 μL once before removing all supernatant and drying at room temperature with open tube cap. Deionized water 50 μL or 0.5× TBE buffer solution was added to fully resolute DNA. Finally, DNA gel electrophoresis was performed for the abovementioned DNA sample. The DNA ladder electrophoresis chart in FIG. 16 confirmed the result from TUNEL test. DNA fragmentation occurred in K-562 cells 48 hours after being treated with Tellimagrandin II at different concentrations.

ROS Test

A radical specific fluorescent dye, 2',7'-dichlorofluorescein (DCF-DA) was used to detect $H_2O_2$/NO-based radicals or $O_2$— in cells respectively.

Figure 17:
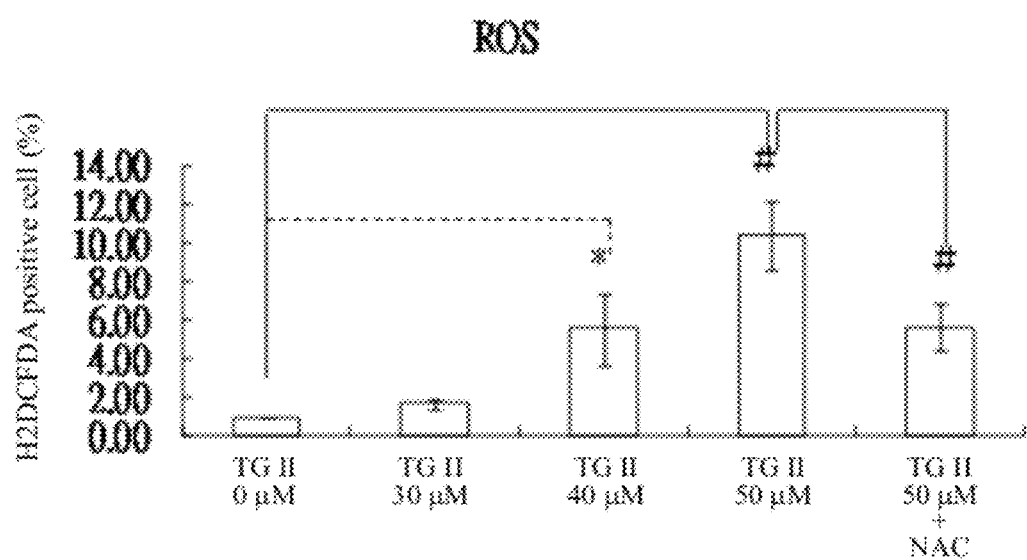
FIG. 17 shows the ROS generation of human erythromyeloblastoid leukemia K-562 cells treated with Tellimagrandin II for 2 hours (N=3, *p<0.05, #p<0.01).

A total of 3 mL cell solution at the concentration of $1\times10^6$ K-562 cells per mL was cultured with 6 cm cell culture plates in an incubator supplied with 5% $CO_2$ at 37° C. for 30 minutes so that cells could adapt to the environment. Tellimagrandin II solutions of different concentrations were added by order so that the final concentrations are 0, 30, 40 and 50 μM respectively. The solution was placed in incubator with 5% $CO_2$ at 37° C. for 2 hours before being centrifuged at 3,500 rpm at 4° C. for 5 minutes and then being rinsed by PBS once. 2',7'-dichlorofluorescein (DCF-DA) was added before the solution was put into dark incubator for 45 minutes and then rinsed by PBS once again. Finally, 1 mL PBS was used to resuspend the cells before BD FACScan was used to detect the fluorescent signal. From the results shown in FIG. 17, ROS in K-562 cells were observed to increase by BD FACScan 2 hours after interaction with 40 μM Tellimagrandin II in ROS test. Besides, an inhibition of ROS production was observed if pre-treated with the anti-oxidant, N-acetyl-L-cysteine, 10 μM before cells interacted with Tellimagrandin II 50 μM for 2 hours (N=3, *p<0.05, #p<0.01).

Western Blotting

A total of 3 mL cell solution at the concentration of $1 \times 10^6$ K-562 cells per mL was cultured in 6 cm cell culture dish in an incubator supplied with 5% $CO_2$ at 37° C. for 30 minutes so that cells could adapt to the environment. Tellimagrandin II solutions of different concentrations were added by order so that the final concentrations are 0, 40 and 50 μM, respectively. The solution was placed in incubator with 5% $CO_2$ at 37° C. for 48 hours. After incubation, it was centrifuged at 1,000 rpm at 4° C. for 5 minutes and rinsed by PBS once. RIPA buffer solution containing protease inhibitors was added to decompose the cells.

The solution was rapidly frozen with liquid nitrogen and unfrozen for three times to ensure that cells had been broken by the physical damages. The solution was centrifuged at 15,000 rpm at 4° C. for 30 minutes; the supernatant containing total cell protein was collected. Protein concentrations were determined by BCA protein assay. Finally, equal amounts of protein samples (40 μg) were boiled in 1× loading buffer for 3 minutes to decompose protein into primary structure for further protein gel electrophoresis (or stored at −80° C.).

SDS-PAGE 10% or 12% was selected by the desired protein molecular weight in the protein gel electrophoresis (150 V, 17 mA for 2 hour and 5 minutes). The protein was transferred from the gel to PVDF membrane using wet transfer procedure (100 V, 300 mA for 30 minutes). The membrane was blocked at room temperature for one hour in Tris-buffered saline-Tween (TBS-T) buffer solution containing 2% Bovine serum albumin (BSA) to eliminate non-specifically binding.

Figure 18:
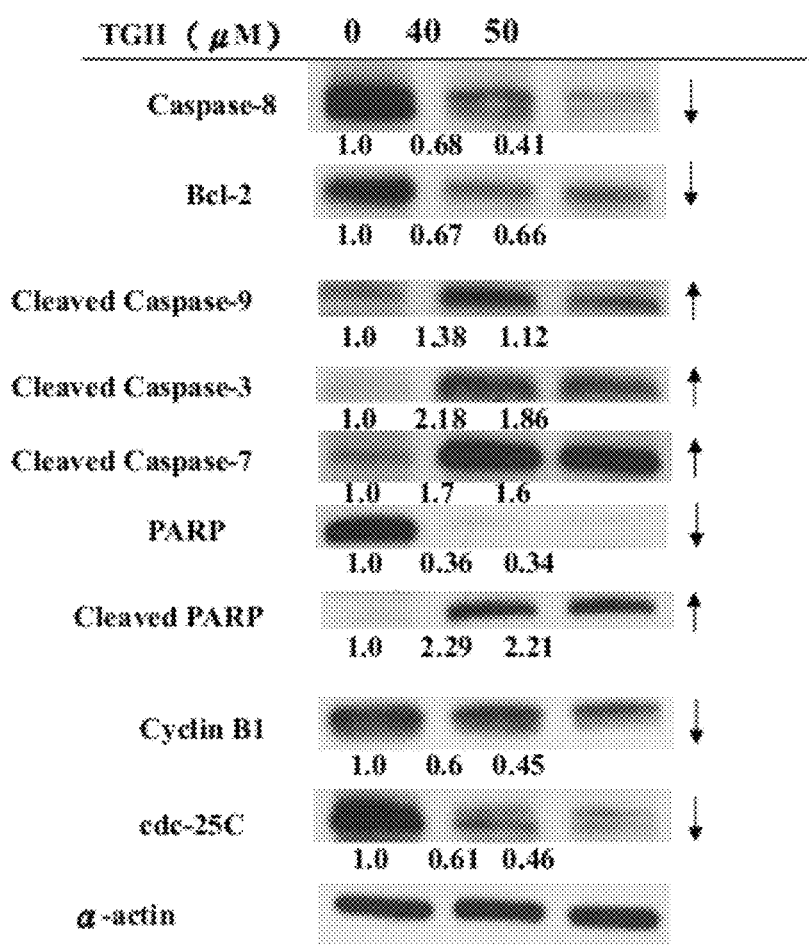
FIG. 18 shows expression of Caspase-8, Bcl-2, Caspase-9, Caspase-3, Caspase-7, PARP, Cyclin B1 and Cdc-25C by western immunoblot in human erythromyeloblastoid leukemia K-562 cells treated or not with Tellimagrandin II for 48 hours (N=3, protein quantification was based on α-actin).

PVDF membrane was probed with primary antibody diluted with by the recommended amount according the manufacture in 2% BSA-TBS-T buffer solution at 4° C. for 16 to 18 hours. After the interaction completed, TBS-T buffer solution was used to rinse out the non-specifically bound primary antibody. TBS-T buffer solution was changed every 10 minutes for three times in about 30 minutes. Then, specific secondary antibody was added for interaction at room temperature for one hour. TBS-T buffer solution was used to rinse out the non-specifically bound secondary antibody. TBS-T buffer solution was changed every 10 minutes for six times in about 60 minutes. ECL System (Enhanced chemiluminescence system) was used and film was exposed to light and developed. Finally qualitative analysis was performed. FIG. 18 indicated that, from the results of Western Blotting, first, inactivity of Cacpase-8 in the external death path decreases, presumably being activated into cleaved Caspase-8. As indicated in the previous result of ROS increase, the result also showed a decrease in the protein of anti-apoptosis Bcl-2, further inducing the activation of Caspase-9, Caspase-3, and Caspase-7 and the ultimate activation of PARP. Protein related to cell cycle regulation includes G2/M checkpoint regulators, Cyclin B1 and Cdc-25C. The result above also found that the (non-phosphorylated) activity decreased after interaction with Tellimagrandin II, confirming the stagnation of cell cycle (N=3, protein quantification was based on α-actin).

Statistical Analysis

Student's t-tests (unpaired) were performed. Results are presented as the mean of at least 3 individual experiments with standard error (mean±S.D.) and P-value≤0.01 or ≤0.05 was considered significant.

One skilled in the art readily appreciates that the present invention is well adapted to carry out the objects and obtain the ends and advantages mentioned, as well as those inherent therein. The animals, processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method of inhibiting growth of Methicillin-resistant *Staphylococcus aureus* in a subject in need thereof comprising administering to the subject an effective amount of Tellimagrandin II together with an oxacillin or a doxycycline, wherein the Tellimagrandin II further comprises its pharmaceutically acceptable salt, enantiomer, isomer or tautomer.

2. The method of claim 1, wherein the Tellimagrandin II acts synergistically with the oxacillin or the doxycycline to inhibit the growth of Methicillin-resistant *Staphylococcus aureus*.

3. The method of claim 1, wherein the Tellimagrandin II has a concentration of more than 30 μg/mL in vivo.

4. The method of claim 2, wherein the Tellimagrandin II and doxycycline act synergistically through an anti-oxidative mechanism.

5. The method of claim 1, wherein the oxacillin acts with Tellimagrandin II to reduce Penicillin-binding protein 2a expression in *Staphylococcus aureus*.

6. The method of claim 1, wherein the oxacillin acts with the Tellimagrandin II to inhibit mecA gene expression in *Staphylococcus aureus*.

7. The method of claim 1, wherein the Tellimagrandin II inhibits *Staphylococcus aureus* biofilm formation.

8. A method of treating leukemia in a subject in need thereof comprising administering to the subject an effective amount of Tellimagrandin II together with its pharmaceutically acceptable salt, enantiomer, isomer or tautomer.

9. The method of claim 8, wherein the Tellimagrandin II induces cell apoptosis and cell cycle arrest of leukemia cell.

10. The method of claim 8, wherein the Tellimagrandin II has a concentration in the range of 20-80 μM in vivo.

11. The method of claim 9, wherein the Tellimagrandin II induces cell apoptosis by increasing intracellular active oxygen species.

12. The method of claim 9, wherein the cell apoptosis of leukemia cell is induced by activating Caspase 3 and Caspase 7.

13. The method of claim 9, wherein the cell cycle arrest of leukemia cell is arrested in G2/M phase.

* * * * *